USO11547380B2

(12) United States Patent
Liu et al.

(10) Patent No.: US 11,547,380 B2
(45) Date of Patent: Jan. 10, 2023

(54) REAL-TIME SPATIAL PRECISE MAGNETIC POSITIONING DEVICE, RADIOGRAPHIC IMAGING SYSTEM AND MAGNETIC POSITIONING METHOD

(71) Applicant: Careray Digital Medical Technology Co., Ltd., Suzhou (CN)

(72) Inventors: Yuhao Liu, Suzhou (CN); Jianqiang Liu, Suzhou (CN)

(73) Assignee: CARERAY DIGITAL MEDICAL TECHNOLOGY CO., LTD., Suzhou (CN)

( * ) Notice: Subject to any disclaimer, the term of this patent is extended or adjusted under 35 U.S.C. 154(b) by 91 days.

(21) Appl. No.: 17/318,503

(22) Filed: May 12, 2021

(65) Prior Publication Data

US 2021/0353246 A1    Nov. 18, 2021

Related U.S. Application Data

(60) Provisional application No. 63/024,007, filed on May 13, 2020.

(30) Foreign Application Priority Data

Jun. 16, 2020  (CN) .......................... 202010547154.8
Dec. 2, 2020  (CN) .......................... 202011391252.3

(51) Int. Cl.
*A61B 6/00*    (2006.01)
*G03B 42/02*   (2021.01)

(52) U.S. Cl.
CPC ............ *A61B 6/587* (2013.01); *A61B 6/4291* (2013.01); *A61B 6/547* (2013.01); *G03B 42/025* (2013.01)

(58) Field of Classification Search
CPC ....... A61B 6/587; A61B 6/547; A61B 6/4291; A61B 2034/2051; A61B 2034/2072;
(Continued)

(56) References Cited

FOREIGN PATENT DOCUMENTS

CN    102262167 A    11/2011
CN    103415252 A    11/2013
(Continued)

OTHER PUBLICATIONS

International Search Report and Written Opinion issued in corresponding International Application No. PCT/CN2020/133372; dated Mar. 16, 2021; State Intellectual Property Office of the P.R. China, Beijing, China, 19 pgs.

*Primary Examiner* — Don K Wong
(74) *Attorney, Agent, or Firm* — Hauptman Ham, LLP

(57) ABSTRACT

A real-time spatial magnetic positioning device, a radiographic imaging system and a magnetic positioning method is provided. The radiographic imaging system comprises a radiation source, a collimator, a flat panel detector, and a real-time spatial magnetic positioning device, wherein the magnetic positioning device comprises a processor, a magnetic field generating device and a magnetic sensor array; the magnetic field generating device is arranged coaxially with the collimator, a plurality of sensors of the magnetic sensor array is distributed on the flat panel detector; the magnetic field generating device is configured to generate an alternating magnetic field, the magnetic sensors are capable of independently detecting magnetic induction intensity in real time, and sending real-time detected data to the processor, and the processor determines a position relationship between the collimator and the flat panel detector according to the data detected by respective magnetic sensors in real time.

12 Claims, 3 Drawing Sheets

(58) Field of Classification Search
CPC ....... A61B 5/0024; A61B 5/062; A61B 5/065; G03B 42/025
See application file for complete search history.

(56) References Cited

FOREIGN PATENT DOCUMENTS

| | | | |
|---|---|---|---|
| CN | 109451773 A | 3/2019 | |
| CN | 110293860 A | 10/2019 | |
| CN | 110602988 A | 12/2019 | |
| DE | 102010008551 A1 | 8/2011 | |
| WO | WO-2020096810 A1 * | 5/2020 | ......... A61B 18/1492 |

* cited by examiner

REAL-TIME SPATIAL PRECISE MAGNETIC POSITIONING DEVICE, RADIOGRAPHIC IMAGING SYSTEM AND MAGNETIC POSITIONING METHOD

CROSS-REFERENCE TO RELATED APPLICATION

This application claims the benefit of priority to U.S. Provisional Patent Application No. 63/024,007, filed May 13, 2020, entitled A Real-Time Magnetic Positioning System, and the benefit of priority to Chinese Patent Application No. 2020105471548, filed Jun. 16, 2020, and the benefit of priority to Chinese Patent Application No. 2020113912523, filed Dec. 2, 2020, which are hereby incorporated by reference herein in its entirety.

FIELD OF TECHNOLOGY

The present disclosure generally relates to a medical equipment positioning field, and more particularly relates to a real-time spatial precise magnetic positioning device, a radiographic imaging system and a magnetic positioning method.

BACKGROUND

The technologies currently used for positioning mainly comprise satellite positioning technology, wireless positioning technology (Wi-Fi positioning, Bluetooth positioning, etc.), environmental characteristic magnetic positioning technology, accelerometer positioning technology, etc.

The satellite positioning technology is to determine location of a positioning point by measuring the electromagnetic wave propagation time difference between the positioning point and different satellites, and then converting it into a distance from the positioning point to the satellite; the wireless positioning technology is to determine a position of a positioning point by measuring the wireless signal strength at the positioning point (the strength of Wi-Fi And Bluetooth and other signals); the environmental characteristic magnetic positioning technology is to determine a location of a positioning point by testing the environmental magnetic field where the positioning point is located, and comparing with a database; the accelerometer positioning technology is to obtain the trajectory of a positioning point by measuring acceleration of an object in real time, and integrating twice in time. At present, according to the field of application, these positioning technologies are combined to complement each other, forming various application schemes.

However, above positioning technologies have their own shortcomings: the satellite positioning technology tests relative position of the positioning point to each satellite, so it requires signals from more than three satellites to be received at the positioning point to determine the position, and it can only be applied outdoors and has a high cost; in addition, because speed of propagation of electromagnetic waves is very fast, even if atomic clock is used for time service, the positioning error is at meter level.

The wireless positioning technology and characteristic magnetic positioning technology can be applied indoors and outdoors, however, due to a need to compare test data of the positioning point with the database, it is necessary to carry out environmental mapping and database establishment before positioning, and can only be applied to known environment, and due to large interference, the positioning accuracy is not high, generally at meter level.

Since the accelerometer positioning technology can only determine relative movement of the test point, other technologies are needed to perform position calibration before starting positioning, such as starting movement at a specified position; in addition, because this technology only tests the acceleration over time, its error accumulates with increase of time, and generally, the positioning accuracy exceeds one meter after a few minutes.

However, the positioning accuracy of medical equipment needs to be at centimeter level, and there is no precise positioning technology that can be applied to medical equipment in an indoor environment in the conventional art.

SUMMARY

A real-time spatial magnetic positioning device, a radiographic imaging system and a magnetic positioning method, which can be used indoors and have a positioning accuracy at centimeter level or even less than one centimeter, and technical solutions are as follows:

In one aspect, the present disclosure provides a real-time spatial magnetic positioning device for realizing the alignment of a first object to a reference area on a second object, the magnetic positioning device comprises a processor, a magnetic field generating device arranged coaxially with the first object, and a magnetic sensor array arranged on the second object, wherein the magnetic field generating device at least comprises an alternating magnetic field generator for generating an alternating magnetic field, and the magnetic sensor array is configured such that a distance from each magnetic sensor of the magnetic sensor array to a center point of the reference area is equal;

a plurality of magnetic sensors of the magnetic sensor array are capable of independently detecting magnetic induction intensity in real time, and sending real-time detected magnetic induction intensity data to the processor, and the processor is configured to compare values of the magnetic induction intensity detected in real time by respective magnetic sensors;

the position of the first object and/or the second object is configured to be adjusted until it is determined that the first object at a current position is aligned with the reference area on the second object after a comparison by the processor, if the magnetic induction intensity detected in real time by more than half of the magnetic sensors is equal, or differences of the magnetic induction intensity are less than a preset threshold or a proportional threshold.

Further, the magnetic field generating device further comprises a bias magnet for biasing the magnetic sensors to a preset operating magnetic field range, and the bias magnet is a permanent magnet or an electromagnet.

Further, the alternating magnetic field generator is capable of performing magnetic field encoding, and the magnetic field generating device is capable of bidirectional communication with the magnetic sensor array.

Further, the alternating magnetic field generator is configured to adjust the intensity of the magnetic field generated by itself according to the relative position relationship between the first object and the reference area on the second object.

Further, the alternating magnetic field generator is configured to be any one of the following three manners:

the alternating magnetic field generator comprises three orthogonal modulation coils, and by modulating the coil current, the magnetic field generated by the magnetic field generating device can change in the size and/or direction of the magnetic field in a three-dimensional space; or, the alternating magnetic field generator comprises a first modulation coil and a second modulation coil at a preset angle, and the two modulation coils work alternately; if the sensor is at a position where the magnetic field gradient of the first coil is less than 0.01 mT/m, the magnetic field gradient generated by the second coil at the position of the sensor must be greater than 0.01 mT/m due to the two coils have a preset angle, and at this moment, the magnetic field sensors obtain the relative position relationship between the first object and the second object depending on the magnetic field generated by the second coil; or, the alternating magnetic field generator comprises a permanent magnet and a mechanical transmission device for driving the permanent magnet to move, wherein the permanent magnet generates an alternating magnetic field in space under the drive of the mechanical transmission device, and the magnetic field can be modulated by the mechanical transmission device.

Further, the alternating magnetic field generator and the sensor array are respectively provided with an angle sensor, and the angle sensors are respectively used to calculate the azimuth angles of the first object and the second object while the magnetic sensors carry out magnetic field measurement, to determine the attitude between the first object and the second object.

Further, the alternating magnetic field generator and the sensor array are respectively provided with an acceleration sensor, and the acceleration sensors are respectively used to calculate three-dimensional acceleration data of the first object and the second object while the magnetic sensors carry out magnetic field measurement, to determine the acceleration, velocity and relative position relationship of the first object and the second object.

As another technical solution, the present disclosure further provides a real-time spatial magnetic positioning device for determining a position relationship between a first object and a reference area on a second object, the magnetic positioning device comprises a processor, a magnetic field generating device arranged coaxially with the first object, and a magnetic sensor array arranged on the second object, wherein the magnetic field generating device at least comprises an alternating magnetic field generator for generating an alternating magnetic field, and the magnetic sensor array is configured such that set positions of a plurality of magnetic sensors thereof have a certain position relationship with a center point of the reference area;

a plurality of magnetic sensors of the magnetic sensor array are capable of independently detecting magnetic induction intensity in real time, and sending a real-time detected magnetic induction intensity data to the processor, and the processor is configured to calculate a position coordinate of respective magnetic sensors relative to the magnetic field generating device according to the magnetic induction intensity data;

the processor is configured to calculate a position coordinate of the center point of the reference area relative to the first object based on the position coordinates of more than half of the magnetic sensors relative to the magnetic field generating device and position relationships between the magnetic sensors and the center point of the reference area.

Further, the position coordinate of the center point of the reference area relative to the first object calculated by the processor is a three-dimensional coordinates of x/y/z coordinate axes, and the processor is configured to analyze the three-dimensional coordinate: if the coordinates of two coordinate axes parallel to a plane where the first object is located are 0 or within a preset range close to 0, it is determined that the first object at the current position is aligned with the reference area on the second object.

Further, the magnetic field generating device further comprises a bias magnet for biasing the magnetic sensors to a preset operating magnetic field range, and the bias magnet is a permanent magnet or an electromagnet.

Further, the alternating magnetic field generator is capable of performing magnetic field encoding, and the magnetic field generating device is capable of bidirectional communication with the magnetic sensor array.

Further, the alternating magnetic field generator is configured to adjust the intensity of the magnetic field generated by itself according to the relative position relationship between the first object and the reference area on the second object.

Further, the alternating magnetic field generator is configured to be any one of the following three manners:

the alternating magnetic field generator comprises three orthogonal modulation coils, and by modulating the coil current, the magnetic field generated by the magnetic field generating device can change in the size and/or direction of the magnetic field in a three-dimensional space; or, the alternating magnetic field generator comprises a first modulation coil and a second modulation coil at a preset angle, and the two modulation coils work alternately; if the sensor is at a position where the magnetic field gradient of the first coil is less than 0.01 mT/m, the magnetic field gradient generated by the second coil at the position of the sensor must be greater than 0.01 mT/m due to the two coils have a preset angle, and at this moment, the magnetic field sensors obtain the relative position relationship between the first object and the second object depending on the magnetic field generated by the second coil; or, the alternating magnetic field generator comprises a permanent magnet and a mechanical transmission device for driving the permanent magnet to move, wherein the permanent magnet generates an alternating magnetic field in space under the drive of the mechanical transmission device, and the magnetic field can be modulated by the mechanical transmission device.

Further, the alternating magnetic field generator and the sensor array are respectively provided with an angle sensor, and the angle sensors are respectively used to calculate the azimuth angles of the first object and the second object while the magnetic sensors carry out magnetic field measurement, to determine the attitude between the first object and the second object.

Further, the alternating magnetic field generator and the sensor array are respectively provided with an acceleration sensor, and the acceleration sensors are respectively used to calculate three-dimensional acceleration data of the first object and the second object while the magnetic sensors carry out magnetic field measurement, to determine the acceleration, velocity and relative position relationship of the first object and the second object.

In another aspect, the present disclosure provides a radiographic imaging system with a magnetic positioning function, the system comprises a radiation source, a collimator, a flat panel detector, and a real-time spatial magnetic positioning device, wherein the magnetic positioning device comprises a processor, a magnetic field generating device and a magnetic sensor array, the magnetic field generating device is arranged coaxially with the collimator, a plurality of sensors of the magnetic sensor array is distributed on the flat panel detector;

the magnetic field generating device at least comprises an alternating magnetic field generator for generating an alternating magnetic field, the magnetic sensors of the magnetic sensor array is capable of independently detecting magnetic induction intensity in real time, and sending the real-time detected magnetic induction intensity data to the processor, and the processor determines the position relationship between the collimator and the flat panel detector according to the magnetic induction intensity detected by the respective magnetic sensors in real time.

In another aspect, the present disclosure provides a first real-time spatial magnetic positioning method, comprising following steps:

S11, arranging a magnetic field generating device coaxially with a first object, setting a reference area to be aligned on a second object, and determining a center point of the reference area; and arranging a plurality of magnetic sensors on the second object where a distance from each magnetic sensor to the center point is equal;

S12, generating an alternating magnetic field by the magnetic field generating device, and independently detecting magnetic induction intensity in real time by the magnetic sensors;

S13, comparing the magnetic induction intensity detected in real time by the magnetic sensors;

S14, determining that the first object at a current position is aligned with the reference area on the second object if the magnetic induction intensity detected in real time by more than half of the magnetic sensors is equal, or differences of the magnetic induction intensity are less than a preset threshold or a proportional threshold, and ending positioning; otherwise, proceeding S15;

S15, adjusting position of the first object and/or the second object, and repeating Steps S12-S14.

In another aspect, the present disclosure provides a second real-time spatial magnetic positioning method, comprising following steps:

S21, arranging a magnetic field generating device coaxially with a first object, setting a reference area to be aligned on a second object, and determining a center point of the reference area; and arranging a plurality of magnetic sensors on the second object, and acquiring a position relationship between each magnetic sensor and the center point;

S22, generating an alternating magnetic field by the magnetic field generating device, and independently detecting magnetic induction intensity in real time by the magnetic sensors;

S23, calculating a position coordinate of the each magnetic sensor relative to the magnetic field generating device according to detection data of the magnetic induction intensity;

S24, excluding one or less than half of the magnetic sensors as an interfered magnetic sensor if the position coordinate of the one or less than half of the magnetic sensors deviate from a plane determined by the position coordinates of remaining magnetic sensors, and obtaining the position coordinate of the center point relative to the first object only according to the position coordinates of the remaining magnetic sensors relative to the magnetic field generating device and position relationships between the remaining magnetic sensors and the center point;

S25, determining that the first object at a current position is aligned with the reference area on the second object if in a three-dimensional coordinate of x/y/z coordinate axes of the center point relative to the first object, the coordinates of two coordinate axes parallel to a plane where the first object is located are 0 or within a preset range close to 0, and ending positioning; otherwise, proceeding S26;

S26, adjusting position of the first object and/or the second object, and repeating Steps S22-S25.

In another aspect, the present disclosure provides a third real-time spatial magnetic positioning method, comprising following steps:

S31, arranging two coils of a magnetic field generator at a preset angle on a first object, wherein the preset angle is not equal to 90°, setting a reference area to be aligned on a second object, and determining a center point of the reference area; and arranging a plurality of magnetic sensors on the second object, and acquiring a position relationship between each magnetic sensor and the center point;

S32, generating an alternating magnetic field by alternatively operating two coils of the magnetic field generator, and independently detecting magnetic induction intensity in real time by the sensors;

S33, counting one set when the two coils alternatively operate one time, dividing detection data of the magnetic induction intensity into several groups; respectively calculating a position coordinate of each magnetic sensors relative to the magnetic field generator according to the detection data of the magnetic induction intensity;

S34, if difference between two position coordinates in one group exceeds a preset threshold, discarding one position coordinate data with a larger offset by comparing with the data detected by other magnetic sensors;

S35, obtaining the position coordinates of the center point relative to the first object according to the remaining position coordinate data after processed in S34 and the position relationships between the remaining magnetic sensors and the center point;

S36, determining that the first object at the current position is aligned with the reference area on the second object if in a three-dimensional coordinate of x/y/z axes of the center point relative to the first object, the coordinates of two coordinate axes parallel to a plane where the first object is located are 0 or within a preset range close to 0, and ending positioning; otherwise, proceeding S37;

S37, adjusting the position of the first object and/or the second object, and repeating Steps S32-S36.

In addition, the present disclosure further provides a real-time spatial magnetic positioning correction method, comprising following steps:

S41, calculating a relative position of a first object relative to a second object at time t0 from a three-dimensional magnetic field data of magnetic sensors, according to the magnetic positioning method as described above;

S42, at time t1, obtaining three-dimensional magnetic field data, three-dimensional acceleration data, and three-dimensional attitude data at time t1, respectively through a magnetic sensor, an accelerometer, and an angle sensor;

S43, calculating a relative position pt1 of the first object relative to the second object at time t1 according to the three-dimensional magnetic field data and three-dimensional attitude data at time t1; calculating a relative speed v1 of the first object relative to the second object at time t1 according to the three-dimensional acceleration data at time t1;

S44, at time t2, obtaining three-dimensional magnetic field data, three-dimensional acceleration data, and three-dimensional attitude data at time t2, respectively through the magnetic sensor, the accelerometer, and the angle sensor;

S45, calculating the relative position pt2 of the first object relative to the second object at time t2 according to the three-dimensional magnetic field data and three-dimensional attitude data at time t2; calculating the relative position pt2' of the first object relative to the second object at time t2 according to the three-dimensional acceleration data at time t2 and the relative speed v1 at time t1;

S46, comparing pt2 and pt2', and determining the relative position of the first object relative to the second object at time t2 is the mean value of pt2 and pt2' if the error between the two is within 1 cm, otherwise proceeding S47-S48;

S47, comparing the three-dimensional acceleration data at time t2 with the speed v1 at time t1, determining the relative position of the first object relative to the second object at time t2 is pt2 if both the speed v1 and the three-dimensional acceleration are approximately 0, otherwise the relative position of the first object relative to the second object at time t2 is pt2';

S48, adjusting the position of the first object and/or the second object, and repeating Steps S41-S46.

The beneficial effects brought about by the technical solution provided in the present disclosure are as follows:

a. The positioning accuracy is less than 1cm within a space of several meters;

b. Strong anti-interference ability is provided;

c. The cost is controllable, which is suitable for positioning and alignment of devices widely used in the fields of industrial control and medical equipment.

BRIEF DESCRIPTION

Some of the embodiments will be described in detail, with references to the following Figures, wherein like designations denote like members, wherein.

Wherein, the references are as follows: 1—first object, 2—second object, 31—alternating magnetic field generator, 32—bias magnet, 4—magnetic sensor.

DETAILED DESCRIPTION

In order to enable those skilled in the art to better understand the solutions of the present disclosure, the technical solutions in the embodiments of the present disclosure are explained clearly and completely below in conjunction with the accompanying drawings, and apparently, the described embodiments are merely a part of the embodiments of the present disclosure, not all the embodiments. Based on the embodiments of the present disclosure, all other embodiments obtained by one of ordinary skill in the art without creative work fall within the protective scope of the present disclosure.

It should be noted that terms "first", "second" and the like in the description, the claims and the accompanying drawings of the present disclosure are used to distinguish similar objects, and do not have to be used to describe a specific order or sequence. It should be understood that the data so used can be interchanged under appropriate circumstances so that the embodiments of the present disclosure described herein can be implemented in an order other than those illustrated or described herein. In addition, the terms "comprise" and "have" and any variations thereof are intended to cover non-exclusive inclusions, for example, processes, methods, devices, products or equipment that include a series of steps or units are not necessarily limited to those clearly listed steps or units, but may include other steps or units not explicitly listed or inherent to these processes, methods, products or equipment.

The present disclosure puts forward a high-precision positioning scheme that uses a single magnet or a magnet array to cooperate with a magnetic sensor array. The magnet/magnet array comprises one or more permanent magnets or electromagnets or a combination thereof, the magnetic sensor array comprises a plurality of magnetic field sensors. In one embodiment, the magnet/magnet array can communicate wirelessly with the magnetic sensor array. This technology can provide a positioning accuracy of less than one centimeter within a range of several meters, which fills the gap of centimeter-level precision positioning, and has a wide range of applications in industrial control and medical equipment.

Figure 1:
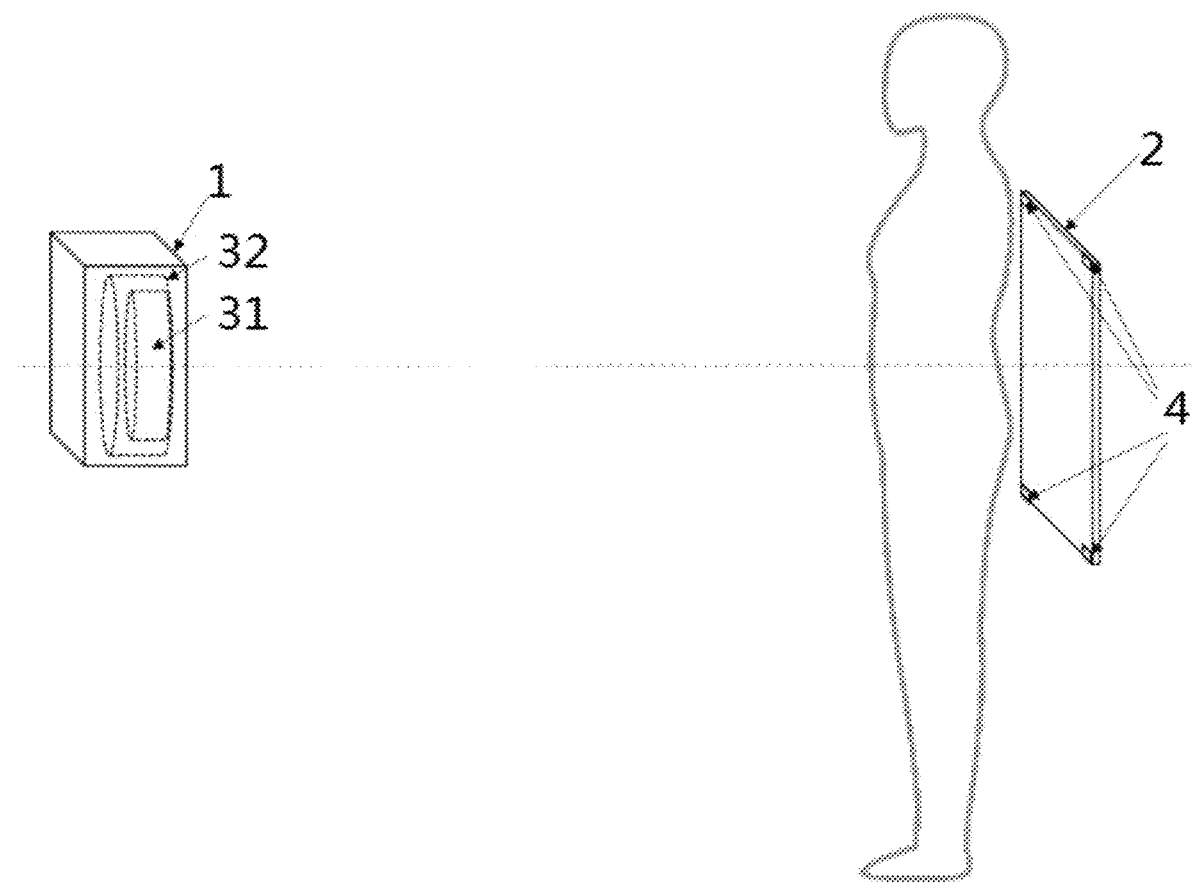
FIG. 1 is a schematic diagram of the installation and application of a real-time spatial magnetic positioning device in a radiographic imaging system according to an embodiment of the present disclosure.
Figure 3:
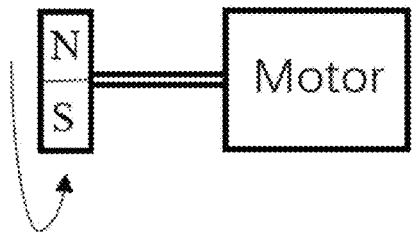
FIG. 3 is a schematic structure diagram of an alternating magnetic field generator comprising a mechanical transmission device and a permanent magnet in a magnetic positioning device provided by an embodiment of the present disclosure.

In one embodiment of the present disclosure, a real-time spatial magnetic positioning device is provided, which is used for realizing an alignment of a first object 1 to a reference area on a second object 2, as shown in FIG. 1, the magnetic positioning device comprises a processor, a magnetic field generating device arranged coaxially with the first object 1, and a magnetic sensor array arranged on the second object 2, the magnetic field generating device at least comprises an alternating magnetic field generator 31 for generating an alternating magnetic field, and the magnetic sensor array is configured such that a distance from each magnetic sensor 4 of the magnetic sensor array to a center point of the reference area is equal. Specifically, the alternating magnetic field generator 31 may have various forms:

In one embodiment of the present disclosure, the alternating magnetic field generator 31 comprises a permanent magnet and a mechanical transmission device for driving the permanent magnet to move, and the magnetic field can be modulated by the mechanical transmission device, for example, the permanent magnet is fixed on a motor, as shown in FIG. 3, the permanent magnet can generate an alternating magnetic field in space when the motor drives the permanent magnet to rotate at a certain speed. By controlling the speed of the motor, the spatial magnetic field can be modulated. Further, the permanent magnet may be combined with a coil, so that advantages of the permanent magnet such as strong magnetic field and no power consumption are complementary and combined with the advantages of coil magnetic field such as convenient control, thereby reducing costs and improving positioning accuracy.

Figure 2:
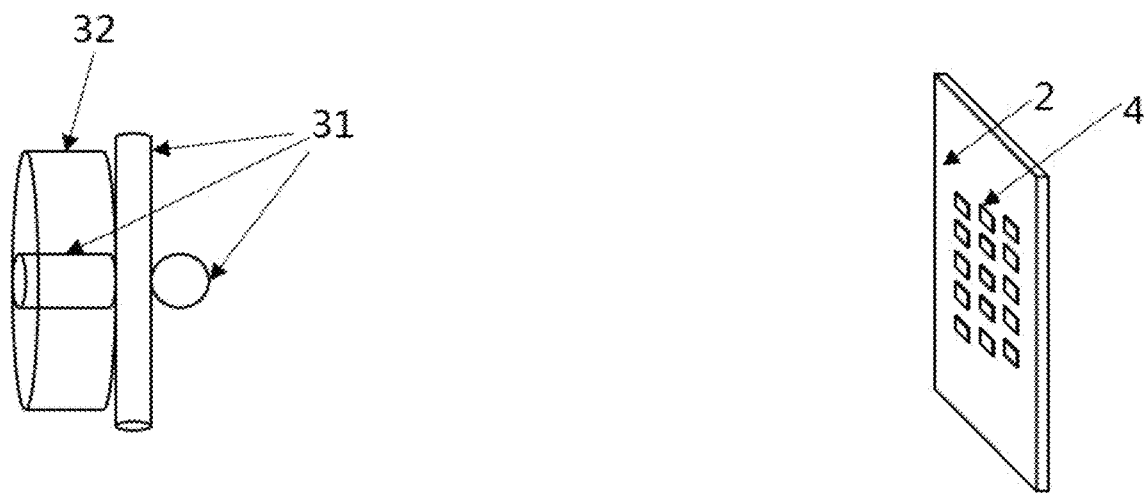
FIG. 2 is a schematic structure diagram of an alternating magnetic field generator comprising three orthogonal modulation coils in a magnetic positioning device provided by an embodiment of the present disclosure.

In another embodiment of the present disclosure, the alternating magnetic field generator 31 comprises three orthogonal modulation coils, as shown in FIG. 2, by modulating the coil current, the magnetic field generated by the magnetic field generating device can change in the size and/or direction of the magnetic field in a three-dimensional space. In this case, the following positioning methods can be used:

One possible positioning method is scanning. The magnetic field generated by the magnetic field generating device scans at a certain speed in three-dimensional space. When an axis of a magnetic sensor in the magnetic sensor array is exactly parallel to it, its value reaches a maximum. Since the magnetic sensor array and the magnetic field generating device can communicate with each other, the magnetic sensor array can calculate its position relative to the magnetic field generating device after scanning the magnetic field in entire space once.

Another possible positioning method is guiding. First, the magnetic sensors complete a search in entire space to find position of the magnetic sensors. Then the magnetic field generating device only scans in a small range to ensure that its direction (not necessarily the direction of the magnetic field, but only a conceptual direction, such as the opposite direction of the magnetic field, the vertical direction of the magnetic field, etc.) always points to the magnetic sensor array. Since there is no need to scan the magnetic field in entire space every time, this method can greatly improve the efficiency of positioning.

In addition to the alternating magnetic field generator, in an embodiment of the present disclosure, the magnetic field generating device further comprises a bias magnet 32 for biasing the magnetic sensors 4 to a preset operating magnetic field range, and the bias magnet 32 is a permanent magnet or an electromagnet. Specifically, the magnetic field generating device generates a non-uniform magnetic field in space, which comprises two parts: one part is a bias magnet field, this part of the magnetic field is generated by a permanent magnet or an electromagnet, and is used to bias the magnetic sensors to a suitable operating magnetic field range; the other part is an alternating magnetic field, which is generated by an alternating current coil or a moving magnet, frequency of the alternating magnetic field can be controlled by controlling the alternating current or the movement frequency of the mechanical structure that controls the movement of the magnet to perform magnetic field encoding. It should be noted that the bias magnetic field can be integrated in the alternating magnetic field generator, that is, a constant current is superimposed on the alternating current; if the magnetic sensor does not require a bias magnetic field to perform high-precision measurement, the bias magnet 32 can also be omitted.

A plurality of magnetic sensors 4 of the magnetic sensor array can independently detect magnetic induction intensity in real time, and send the real-time detected magnetic induction intensity data to the processor, and the processor compares the magnetic induction intensity data detected by the respective magnetic sensors 4 in real time;

The position of the first object 1 and/or the second object 2 is adjusted until: after comparison by the processor, result is obtained that magnetic induction intensity data detected in real time by more than half of the magnetic sensors is the same or the difference between detected magnetic induction intensity is less than a preset threshold or a proportional threshold, specifically for example, if magnetic induction intensity difference between a maximum magnetic induction intensity and a minimum magnetic induction intensity is less than 1 mGs, or the ratio of magnetic induction intensity difference to a current average magnetic induction intensity is less than 1%, it is determined that the first object 1 at a current position is aligned with the reference area on the second object 2.

Specifically, the second object 2 preferably has a flat surface, and the reference area to be aligned with the first object 1 is provided on the flat surface, and the center point of the reference area is determined. Taking the application of the magnetic positioning device in a radiographic imaging system as an example, the radiographic imaging system comprises a radiation source, a collimator, and a flat panel detector, wherein the magnetic positioning device comprises a processor, a magnetic field generating device and a magnetic sensor array, the magnetic field generating device of the magnetic positioning device is arranged coaxially with the collimator (namely, the collimator is the first object 1), one bias coil and one alternating magnetic field coil can be selected and arranged coaxially, in this configuration, the magnet will generate a centrosymmetric spatial magnetic field with the X-ray beam as the axis in space; a plurality of magnetic sensors 4 of the magnetic sensor array are distributed on the flat panel detector (namely, the flat panel detector is the second object 2), and it is not limited to the number and position of the magnetic sensors 4 as four magnetic sensors 4 are located at the four corners of a flat panel as shown in FIG. 1.

As shown in FIG. 1, taking the arrangement of the four magnetic sensors as an example, when the positioning starts, the four magnetic sensors work at the same time, and the amplitude of the magnetic field generated by the magnetic field generator is demodulated through a phase-locked filtering and amplification technology. According to the amplitude, the positions of the respective magnetic sensors relative to the collimator can be calculated. Due to the use of 4 magnetic sensors, if one of them is interfered so as that the magnetic field amplitude test is inaccurate, the position of the flat panel can also be determined through the remaining three (magnetic sensors). In order to further improve the anti-interference ability of the system, an array comprising more magnetic sensors can be provided, for example, eight magnetic sensors can be provided to form an array, and the position could still be positioned accurately if (at most) three sensors operate in interference, relevant details are as follows.

The flat panel detector needs to be close to the area to be photographed when shooting, and center line of the X-ray beam is required to be aligned and perpendicular to the center area of the flat panel detector (the area near the center of the flat panel). This requires physician to accurately determine the placing position of the flat panel detector relative to the X-ray source (collimator), and the magnetic positioning technical solution provided by the embodiment of the present disclosure can provide positioning guidance to the physician, main inventive concept is as follows: the magnetic field generating device at least comprises an alternating magnetic field generator for generating an alternating magnetic field, a plurality of magnetic sensors of the magnetic sensor array can independently detect magnetic induction intensity in real time, and send the real-time detected magnetic induction intensity data to the processor, and the processor is configured to determine the position relationship between the collimator and the flat panel detector according to the magnetic induction intensity data detected by the respective magnetic sensors in real time.

In order to further improve the reliability of positioning, the alternating magnetic field generator 31 can perform magnetic field encoding, the magnetic field generating device and the magnetic sensor array can communicate bidirectionally, and the alternating magnetic field generator 31 can adjust the magnetic field intensity generated by itself according to the determined relative position of the first object and the second object for several times; the method for determining the relative position of the two objects (the first object and the second object) is specifically described as follows, for example, the magnetic field intensity generated by the alternating magnetic field generator 31 could be adjusted: if the magnetic sensor array senses that the magnetic field of each axis of each magnetic sensor is weak, the magnetic sensor array can notify the magnetic field generating device through wireless communication, that is, the magnetic field generating device is notified to increase the magnetic field intensity; on the contrary, if the magnetic field magnetic sensor array senses that the magnetic field is too strong and exceeds its measuring range, the magnetic field generating device is notified to reduce the magnetic field.

Figure 4:
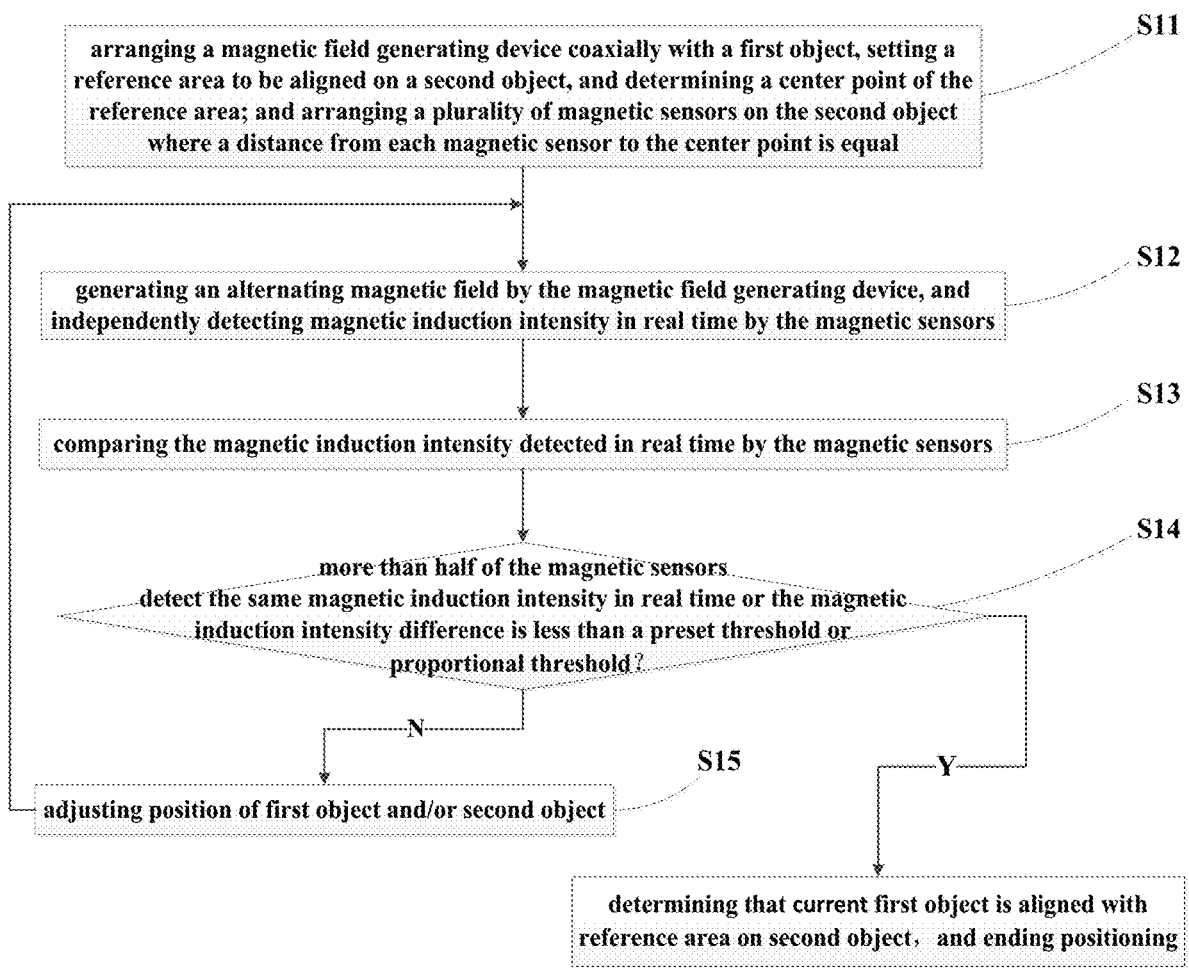
FIG. 4 is flowchart of a first magnetic positioning method provided by an embodiment of the present disclosure.

In an embodiment of the present disclosure, a real-time spatial magnetic positioning method is provided, as shown in FIG. 4, the magnetic positioning method comprises following steps:

S11, arranging a magnetic field generating device coaxially with a first object, setting a reference area to be aligned on a second object, and determining a center point of the reference area; and arranging a plurality of magnetic sensors on the second object where a distance from each magnetic sensor to the center point are the same;

S12, generating an alternating magnetic field by the magnetic field generating device, and independently detecting the magnetic induction intensity in real time by the magnetic sensors;

S13, comparing the magnetic induction intensity data detected by the magnetic sensors in real time;

S14, determining that the first object at a current position is aligned with the reference area on the second object if the magnetic induction intensity data detected in real time by more than half of the magnetic sensors is equal, or differences of the magnetic induction intensity data are less than a preset threshold or a proportional threshold, then ending positioning; otherwise, proceeding S15;

S15, adjusting position of the first object and/or the second object, and repeating Steps S12-S14.

It can be seen from the above that when all the magnetic sensors are arranged at the same distance from the center point of the reference area to be aligned with the first object on the second object, it can be known from the geometric relationship that one plane can be determined by three points, therefore, the number of the magnetic sensors is greater than or equal to three. In the case of more than or equal to three, only when the magnetic field generating device is directly facing the center of the circle where the three or more magnetic sensors are located, it is possible that the magnetic induction intensity detected by the magnetic sensors in real time are the same. In actual operation, the most ideal situation is that the first object is completely facing the center point of the second object; in a case that a certain deviation is allowed, when difference of the magnetic induction intensity detected by the magnetic sensor in real time is less than a preset threshold or proportional threshold, it should also be used as the basis for determining the alignment, for example, the maximum magnetic induction intensity among the data detected by all the magnetic sensors subtracts the minimum magnetic induction intensity to obtain the magnetic induction intensity difference, and if this magnetic induction intensity difference is less than 1 mGs, or the ratio of the magnetic induction intensity difference to a current average magnetic induction intensity is less than 1%, it is determined that the first object 1 at the current position (within the allowable error range) is aligned with the reference area on the second object 2.

Preferably, the number of magnetic sensors is provided to be three or more, such as four, so that even if one of four magnetic sensors is interfered, the magnetic positioning will not be affected; or eight magnetic sensors are provided, if three of them are interfered, it is still possible to determine whether the first object is aligned with the second object based on the remaining five magnetic sensors that are not interfered. Specifically, for example, if six of the eight magnetic sensors have the same magnitude of magnetic induction intensity detected in real time, but the other two have different values of magnetic induction intensity, it can be determined that the two magnetic sensors are interfered, and the interfered detection results thereof can be ruled out.

The technical solution of the above embodiment limits the distance between each magnetic sensor and the center point to be the same, and under this condition, the distance and coordinate values between the specific magnetic sensors (or center point) and the magnetic field generating device may not be considered. In the following embodiment of the present disclosure, a real-time spatial magnetic positioning device based on another inventive concept is provided for determining a position relationship between a first object 1 and a reference area on a second object 2, the magnetic positioning device comprises a processor, a magnetic field generating device arranged coaxially with the first object 1, and a magnetic sensor array arranged on the second object 2, the magnetic field generating device at least comprises an alternating magnetic field generator 31 for generating an alternating magnetic field, and the magnetic sensor array is configured such that the set positions of a plurality of magnetic sensors 4 thereof have a certain position relationship with a center point of the reference area;

In this embodiment, the positions of the magnetic sensors 4 have be arranged discretionarily, and then the position relationship between the magnetic sensors 4 and the center point could be determined. For example, in a pre-established coordinate system, taking a certain magnetic sensor 4 as an origin, the coordinate of the center point is (x1, y1, z1); or taking the center point as an origin, the coordinate of a certain magnetic sensor 4 is (x1', y1', z1').

A plurality magnetic sensors 4 of the magnetic sensor array can independently detect magnetic induction intensity in real time, and send the real-time detected magnetic induction intensity data to the processor, and since the frequency of the magnetic field change is known, technologies such as phase-locked amplification can be used to filter and suppress noise to obtain high-precision magnetic field measurement values, and the processor may obtain the positions of the magnetic sensors relative to the magnetic field generating device, that is, the position coordinates of the respective magnetic sensors 4 relative to the magnetic field generating device through corresponding calculations according to the detection results of the respective magnetic sensors. The position coordinates here are based on the same coordinate system as the above (the coordinate system with the same x/y/z axis direction is called the same coordinate system), with the magnetic field generating device as an origin, and the coordinate of the certain magnetic sensor is (x2, y2, z2), then the coordinate of the center point relative to the magnetic field generator is (x1+x2, y1+y2, z1+z2); or with the certain magnetic sensor as an origin, and the coordinates of the magnetic field generating device is (x2', y2', z2'), then the coordinate of the center point relative to the magnetic field generator is (x1'+x2', y1'+y2', z1'+z2').

Specifically, the magnetic field amplitude can be obtained by real-time detection of the magnetic induction intensity by the magnetic sensor, one of classic algorithms for calculating the position of each magnetic sensor relative to the magnetic field generating device based on the amplitude is the Biot-Savart Law, that is the magnitude of the magnetic induction intensity dB generated by a current element Idl at a certain point P in space is directly proportional to the size of the current element Idl, is directly proportional to the sine of the angle between the position vector from the location of the current element Idl to point P and the current element Idl, and is inversely proportional to the square of the distance from the current element Idl to point P. The classic formula is as follows:

$$d\vec{B} = \frac{\mu_0}{4\pi} \frac{Idl \times \vec{r}}{r^3}$$

$$= \frac{\mu_0}{4\pi} \frac{Idl\sin\theta}{r^2}$$

$$\vec{B} = \int_L \frac{\mu_0 I}{4\pi} \frac{dl \times \vec{e_r}}{r^2},$$

where, I is a source current, L is an integration path, dl is a micro line element of the source current, $\vec{e}_r$ is a unit vector of a current element pointing to the field point to be sought, $\mu_0$, is vacuum permeability, and its value is $4\pi \times 10^{-7}$ N/A$^2$, direction of dB is perpendicular to a plane determined by Idl and $\vec{e}_r$, r is distance between the magnetic sensor and the magnetic field generating device, and $\vec{r}$ is a vector directed from the magnetic sensor to the magnetic field generating device.

The vector $\vec{r}$ calculated by the above formula can be converted into a coordinate in the coordinate system.

If the coil is far enough from the magnetic sensor, the following approximation can be used:

$$\frac{\mu_0}{4\pi}\left(\frac{3(m \cdot r)r}{r^5} - \frac{m}{r^3}\right),$$

where, m=NSIn, where, N is number of turns of the coil, S is area of the coil, I is the current of the coil, and n is direction, which is along the axis of the coil and perpendicular to the coil surface.

In principle, only one magnetic sensor is needed to determine the positional relationship of the center point relative to the magnetic field generating device. However, in order to improve the positioning accuracy and prevent the magnetic sensor from being interfered and causing the wrong positioning result, the magnetic sensor array is preferably provided with three or more magnetic sensors, and if one magnetic sensor is interfered, it will not affect the position determination of the whole array, with high stability.

The processor obtains the position coordinate of the center point of the reference area relative to the first object 1 based on the position coordinates of more than half of the magnetic sensors 4 relative to the magnetic field generating device and the position relationships between the magnetic sensors 4 and the center point of the reference area. For example, the number of the magnetic sensors is six, the coordinates of the center point obtained according to the real-time detection results of four magnetic sensors are all (x', y', z'), but the coordinates of the center point obtained according to the real-time detection results of the other two magnetic sensors are different, it can be determined that the two magnetic sensors are interfered, and the interfered detection results thereof can be ruled out.

For this technical solution of the real-time spatial magnetic positioning device, the processor obtains the position coordinate of the center point of the reference area relative to the first object 1 as three-dimensional coordinate of x/y/z coordinate axes, and the processor analyzes the three-dimensional coordinate, if the coordinates of two coordinate axes parallel to a plane where the first object 1 is located are 0, it is determined that the first object 1 at the current position is aligned with the reference area on the second object 2. In actual operation, it is the most ideal situation that the first object is completely facing the center point of the second object, for example, the coordinate system is established with the magnetic field generating device as an origin, and the center line of the collimator as the x-axis (or as the y-axis or z-axis), then when the coordinate value of the center point is (50, 0, 0), it means that the first object 1 is currently facing the center point of the second object 2; when a certain deviation is allowed, for example, in the coordinate values of the center point, the coordinate values of the y-axis and the z-axis are within a preset range close to 0, such as the range of [−5, +5], for example, the obtained coordinates of the center point corresponding to different magnetic sensors are (50, 5, −5), (50, −5, 5), (50, 5, 5), (50, −5, −5) and so on, it can be determined the first object 1 at the current position (within the allowed error range) is aligned with the reference area on the second object 2.

Same as the previous embodiment, in addition to the alternating magnetic field generator, the magnetic field generating device of this embodiment further comprises a bias magnet 32 for biasing the magnetic sensors 4 to a preset operating magnetic field range, and the bias magnet 32 is a permanent magnet or an electromagnet.

In order to further improve the reliability of positioning, the alternating magnetic field generator 31 can perform magnetic field encoding; the magnetic field generating device and the magnetic sensor array can communicate bidirectionally, and the alternating magnetic field generator 31 can adjust the magnetic field intensity generated by the alternating magnetic field generator according to the determined relative position of the first object and the second object for several times, for example, when the magnetic sensor array senses that the magnetic field of each axis of each magnetic sensor is weak, the magnetic sensor array can notify the magnetic field generating device through wireless communication, that is the magnetic field generating device is notified to increase the magnetic field intensity; on the contrary, when the magnetic field magnetic sensor array senses that the magnetic field is too strong and exceeds its measuring range, the magnetic field generating device is notified to reduce the magnetic field.

Figure 5:
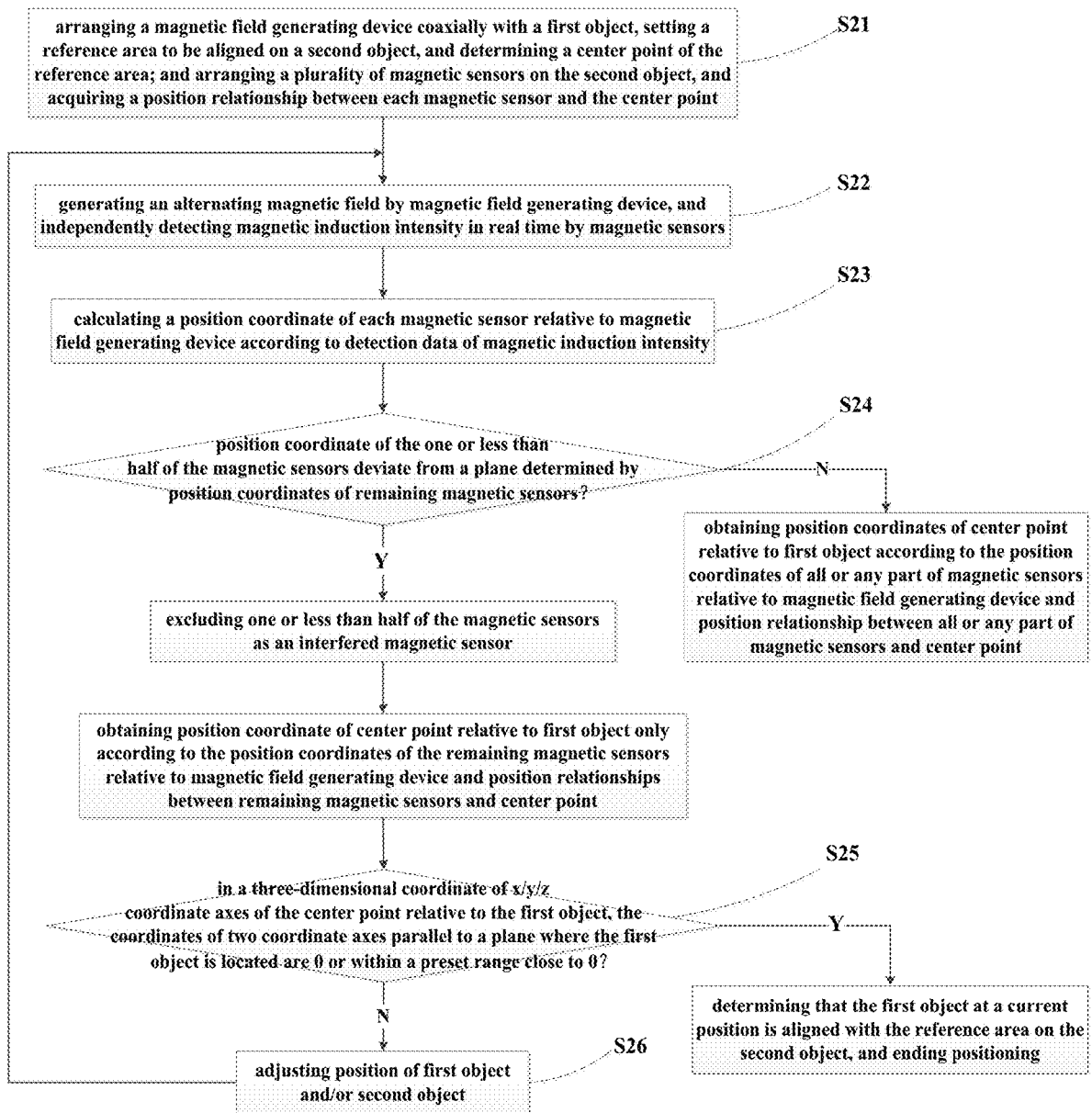
FIG. 5 is flowchart of a second magnetic positioning method provided by an embodiment of the present disclosure.

In an embodiment of the present disclosure, another real-time spatial magnetic positioning method is provided, as shown in FIG. 5, it comprises following steps:

S21, arranging a magnetic field generating device coaxially with a first object, setting a reference area to be aligned on a second object, and determining a center point of the reference area; and arranging a plurality of magnetic sensors on the second object, and acquiring the position relationship between the respective magnetic sensors and the center point;

S22, generating an alternating magnetic field by the magnetic field generating device, and independently detecting the magnetic induction intensity in real time by the magnetic sensors;

S23, calculating the position coordinates of the respective magnetic sensors relative to the magnetic field generating device according to the detection data of the magnetic induction intensity;

S24, excluding one or less than half of the magnetic sensors as the interfered magnetic sensors if the position coordinates of the one or less than half of the magnetic sensors deviate from the plane determined by the position coordinates of the remaining magnetic sensors, and obtaining the position coordinates of the center point relative to the first object only according to the position coordinates of the remaining magnetic sensors relative to the magnetic field generating device and the position relationships between the remaining magnetic sensors and the center point; if there is no deviation, that is, all the magnetic sensors are on the same plane, obtaining the position coordinates of the center point relative to the first object according to the position coordinates of all or any part of the magnetic sensors relative to the magnetic field generating device and the position relationship between all or any part of the magnetic sensors and the center point.

S25, determining that the first object at the current position is aligned with the reference area on the second object if in a three-dimensional coordinate of x/y/z coordinate axes of the center point relative to the first object, the coordinates of two coordinate axes parallel to a plane where the first object is located are 0 or within a preset range close to 0, and ending positioning, specifically see the above for details; otherwise, proceeding S26;

S26, adjusting the position of the first object and/or the second object, and repeating Steps S22-S25.

It should be noted that the above-mentioned magnetic positioning method embodiment belongs to the same concept as the magnetic positioning device provided in the above-mentioned embodiment, for the specific implementation process, please refer to the device embodiment, that is, all the features in the above-mentioned device embodiment can be introduced into the method embodiments by reference.

The embodiment of the present disclosure proposes a third structural form for the alternating magnetic field generator 31, that is the alternating magnetic field generator 31 comprises two modulation coils at a preset angle, the two modulation coils work alternately, and if the magnetic field is located at an area where the gradient of one coil is less than 0.01 mT/m, the relative position between the first object 1 and the second object 2 can be obtained according to another coil.

Specifically, the alternating magnetic field generator 31 and the sensor array each have an angle sensor, and the angle sensors are respectively used to calculate the azimuth angles of the first object 1 and the second object 2 while the magnetic sensors are measuring the magnetic field, to determine the attitude between two objects; and/or the alternating magnetic field generator 31 and the sensor array each have an acceleration sensor, and the acceleration sensors are respectively used to calculate three-dimensional acceleration data of the first object 1 and the second object 2 while the magnetic sensors are measuring the magnetic field, to determine the acceleration, velocity and relative position of the first object 1 and the second object 2, for correcting the magnetic positioning, and the specific correction method is described in detail below.

The above method for obtaining the relative position between the first object 1 and the second object 2 according to another coil specifically comprises following steps:

S31, arranging two coils of a magnetic field generator at a preset angle on a first object, the preset angle is not equal to 90°, setting a reference area to be aligned on a second object, and determining a center point of the reference area; and arranging a plurality of magnetic sensors on the second object, and acquiring the position relationship between the respective magnetic sensors and the center point;

S32, generating an alternating magnetic field by alternatively operating two coils of a magnetic field generator, and independently detecting the magnetic induction intensity in real time by the magnetic sensors;

S33, counting one set when the two coils alternatively operate one time, dividing the detection data of the magnetic induction intensity into several groups; respectively calculating the position coordinates of the respective magnetic sensors relative to the magnetic field generator according to the detection data of the magnetic induction intensity;

S34, comparing with the data detected by other magnetic sensors, if the difference between the two position coordinates in a group exceeds a preset threshold, discarding position coordinate data with a larger offset;

S35, obtaining the position coordinates of the center point relative to the first object according to the remaining position coordinate data after processed in S34 and the position relationships between the remaining magnetic sensors and the center point;

S36, determining that the first object at the current position is aligned with the reference area on the second object if in a three-dimensional coordinate of x/y/z axes of the center point relative to the first object, the coordinates of two coordinate axes parallel to a plane where the first object is located are 0 or within a preset range close to 0, and ending positioning; otherwise, proceeding S37;

S37, adjusting the position of the first object and/or the second object, and repeating Steps S32-S36.

The method for correcting magnetic positioning described above comprises following steps:

S41, using the magnetic positioning method as described above, using the three-dimensional magnetic field data of the magnetic sensors to calculate the relative position of the first object relative to the second object at time t0;

S42, at time t1, using a magnetic sensor, an accelerometer, and an angle sensor to obtain three-dimensional magnetic field data, three-dimensional acceleration data, and three-dimensional attitude data at time t1, respectively;

S43, calculating a relative position pt1 of the first object relative to the second object at time t1 according to the three-dimensional magnetic field data and three-dimensional attitude data at time t1; calculating a relative speed v1 of the first object relative to the second object at time t1 according to the three-dimensional acceleration data at time t1;

S44, at time t2 (later than t1), using the magnetic sensor, the accelerometer, and the angle sensor to obtain three-dimensional magnetic field data, three-dimensional acceleration data, and three-dimensional attitude data at time t2, respectively;

S45, calculating the relative position pt2 of the first object relative to the second object at time t2 according to the three-dimensional magnetic field data and three-dimensional attitude data at time t2; according to the three-dimensional acceleration data at time t2 and the relative speed v1 at time t1, calculating the relative position pt2' of the first object relative to the second object at time t2;

S46, comparing pt2 and pt2', and determining the relative position of the first object relative to the second object at time t2 is the mean value of pt2 and pt2' if the error between the two is within 1 cm, otherwise proceeding S47-S48;

S47, comparing the three-dimensional acceleration value at time t2 with the velocity v1 at time t1, determining the relative position of the first object relative to the second object at time t2 is pt2 if both the velocity v1 and the three-dimensional acceleration are approximately 0, otherwise it is pt2';

S48, adjusting the position of the first object and/or the second object, and repeating Steps S41-S46.

The present disclosure can allow a plurality of magnetic sensor arrays to be positioned at the same time, that is, to realize the positioning of a plurality of objects. This is because different magnetic sensor arrays can independently communicate with the magnetic field generating device to determine their positions relative to the magnetic field generating device. In order to better control the spatial magnetic field and improve the positioning accuracy, a plurality of magnetic field generators can also be used and placed in different spatial positions.

Some magnetically sensitive devices, such as cardiac pacemakers, cannot be used in magnetic positioning, this is because although a weak magnetic field is used, the magnetic field may still be larger than the geomagnetic field, especially near the magnetic field generating device. For this reason, additional magnetic sensor arrays can be mounted near these magnetic field-sensitive devices. As mentioned above, this technology can use one magnetic field generating device to locate a plurality of magnetic sensor arrays, therefore, the position of magnetic sensitive devices can be determined in real time during positioning, and by actively reducing the magnetic field near the magnetic sensitive device to the level of the geomagnetic field, to guarantee it is not affected.

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

What is claimed is:

1. A real-time spatial magnetic positioning device, used for determining a relative position relationship between a first object and a reference area on a second object, the magnetic positioning device comprises a processor, a magnetic field generating device arranged coaxially with the first object, and a magnetic sensor array arranged on the second object, wherein the magnetic field generating device at least comprises an alternating magnetic field generator for generating an alternating magnetic field, and the magnetic sensor array is configured such that set positions of a plurality of magnetic sensors thereof have a certain position relationship with a center point of the reference area;
a plurality of magnetic sensors of the magnetic sensor array are capable of independently detecting magnetic induction intensity in real time, and sending a real-time detected magnetic induction intensity data to the processor, and the processor is configured to calculate a position coordinate of respective magnetic sensors relative to the magnetic field generating device according to the magnetic induction intensity data;
the processor is configured to calculate a position coordinate of the center point of the reference area relative to the first object based on the position coordinates of more than half of the magnetic sensors relative to the magnetic field generating device and position relationships between the magnetic sensors and the center point of the reference area.

2. The real-time spatial magnetic positioning device according to claim 1, wherein the position coordinate of the center point of the reference area relative to the first object calculated by the processor is a three-dimensional coordinates of x/y/z coordinate axes, and the processor is configured to analyze the three-dimensional coordinate: if the coordinates of two coordinate axes parallel to a plane where the first object is located are 0 or within a preset range close to 0, it is determined that the first object at the current position is aligned with the reference area on the second object.

3. The real-time spatial magnetic positioning device according to claim 1, wherein the magnetic field generating device further comprises a bias magnet for biasing the magnetic sensors to a preset operating magnetic field range, and the bias magnet is a permanent magnet or an electromagnet.

4. The real-time spatial magnetic positioning device according to claim 1, wherein the alternating magnetic field generator is capable of performing magnetic field encoding, and the magnetic field generating device is capable of bidirectional communication with the magnetic sensor array.

5. The real-time spatial magnetic positioning device according to claim 1, wherein the alternating magnetic field generator is configured to adjust the intensity of the magnetic field generated by itself according to the relative position relationship between the first object and the reference area on the second object.

6. The real-time spatial magnetic positioning device according to claim 1, wherein the alternating magnetic field generator is configured to be any one of the following three manners:
the alternating magnetic field generator comprises three orthogonal modulation coils, and by modulating the coil current, the magnetic field generated by the magnetic field generating device can change in the size and/or direction of the magnetic field in a three-dimensional space; or,
the alternating magnetic field generator comprises a first modulation coil and a second modulation coil at a preset angle, and the two modulation coils work alternately; if the sensor is at a position where the magnetic field gradient of the first coil is less than 0.01 mT/m, the magnetic field gradient generated by the second coil at the position of the sensor must be greater than 0.01 mT/m due to the two coils have a preset angle, and at this moment, the magnetic field sensors obtain the relative position relationship between the first object and the second object depending on the magnetic field generated by the second coil; or,
the alternating magnetic field generator comprises a permanent magnet and a mechanical transmission device for driving the permanent magnet to move, wherein the permanent magnet generates an alternating magnetic field in space under the drive of the mechanical transmission device, and the magnetic field can be modulated by the mechanical transmission device.

7. The real-time spatial magnetic positioning device according to claim 1, wherein the alternating magnetic field generator and the sensor array are respectively provided with an angle sensor, and the angle sensors are respectively used to calculate the azimuth angles of the first object and the second object while the magnetic sensors carry out magnetic field measurement, to determine the attitude between the first object and the second object.

8. The real-time spatial magnetic positioning device according to claim 1, wherein the alternating magnetic field generator and the sensor array are respectively provided with an acceleration sensor, and the acceleration sensors are respectively used to calculate three-dimensional acceleration data of the first object and the second object while the magnetic sensors carry out magnetic field measurement, to determine the acceleration, velocity and relative position relationship of the first object and the second object.

9. A radiographic imaging system with a magnetic positioning function, comprising a radiation source, a collimator, a flat panel detector, and a real-time spatial magnetic positioning device, wherein the magnetic positioning device comprises a processor, a magnetic field generating device and a magnetic sensor array, wherein the magnetic field generating device is arranged coaxially with the collimator, a plurality of sensors of the magnetic sensor array is distributed on the flat panel detector;

the magnetic field generating device at least comprises an alternating magnetic field generator for generating an alternating magnetic field, a plurality of magnetic sensors of the magnetic sensor array are capable of independently detecting magnetic induction intensity in real time, and sending a real-time detected magnetic induction intensity data to the processor, and the processor is configured to determine a position relationship between the collimator and the flat panel detector according to the magnetic induction intensity data detected by respective magnetic sensors in real time.

10. A real-time spatial magnetic positioning method, comprising following steps:

S21, arranging a magnetic field generating device coaxially with a first object, setting a reference area to be aligned on a second object, and determining a center point of the reference area; and arranging a plurality of magnetic sensors on the second object, and acquiring a position relationship between each magnetic sensor and the center point;

S22, generating an alternating magnetic field by the magnetic field generating device, and independently detecting magnetic induction intensity in real time by the magnetic sensors;

S23, calculating a position coordinate of the each magnetic sensor relative to the magnetic field generating device according to detection data of the magnetic induction intensity;

S24, excluding one or less than half of the magnetic sensors as an interfered magnetic sensor if the position coordinate of the one or less than half of the magnetic sensors deviate from a plane determined by the position coordinates of remaining magnetic sensors, and obtaining the position coordinate of the center point relative to the first object only according to the position coordinates of the remaining magnetic sensors relative to the magnetic field generating device and position relationships between the remaining magnetic sensors and the center point;

S25, determining that the first object at a current position is aligned with the reference area on the second object if in a three-dimensional coordinate of x/y/z coordinate axes of the center point relative to the first object, the coordinates of two coordinate axes parallel to a plane where the first object is located are 0 or within a preset range close to 0, and ending positioning; otherwise, proceeding S26;

S26, adjusting position of the first object and/or the second object, and repeating Steps S22-S25.

11. The real-time spatial magnetic positioning method according to claim 10, further comprising following steps:

S31, arranging two coils of a magnetic field generator at a preset angle on a first object, wherein the preset angle is not equal to 90°, setting a reference area to be aligned on a second object, and determining a center point of the reference area;

and arranging a plurality of magnetic sensors on the second object, and acquiring a position relationship between each magnetic sensor and the center point;

S32, generating an alternating magnetic field by alternatively operating two coils of the magnetic field generator, and independently detecting magnetic induction intensity in real time by the sensors;

S33, counting one set when the two coils alternatively operate one time, dividing detection data of the magnetic induction intensity into several groups; respectively calculating a position coordinate of each magnetic sensors relative to the magnetic field generator according to the detection data of the magnetic induction intensity;

S34, if difference between two position coordinates in one group exceeds a preset threshold, discarding one position coordinate data with a larger offset by comparing with the data detected by other magnetic sensors;

S35, obtaining the position coordinates of the center point relative to the first object according to the remaining position coordinate data after processed in S34 and the position relationships between the remaining magnetic sensors and the center point;

S36, determining that the first object at the current position is aligned with the reference area on the second object if in a three-dimensional coordinate of x/y/z axes of the center point relative to the first object, the coordinates of two coordinate axes parallel to a plane where the first object is located are 0 or within a preset range close to 0, and ending positioning; otherwise, proceeding S37;

S37, adjusting the position of the first object and/or the second object, and repeating Steps S32-S36.

12. The real-time spatial magnetic positioning method according to claim 10, further comprising: correcting the real-time spatial magnetic positioning, which comprises following steps:

S41, calculating a relative position of a first object relative to a second object at time t0 from a three-dimensional magnetic field data of magnetic sensors;

S42, at time t1, obtaining three-dimensional magnetic field data, three-dimensional acceleration data, and three-dimensional attitude data at time t1, respectively through a magnetic sensor, an accelerometer, and an angle sensor;

S43, calculating a relative position pt1 of the first object relative to the second object at time t1 according to the three-dimensional magnetic field data and three-dimensional attitude data at time t1; calculating a relative speed v1 of the first object relative to the second object at time t1 according to the three-dimensional acceleration data at time t1;

S44, at time t2, obtaining three-dimensional magnetic field data, three-dimensional acceleration data, and three-dimensional attitude data at time t2, respectively through the magnetic sensor, the accelerometer, and the angle sensor;

S45, calculating the relative position pt2 of the first object relative to the second object at time t2 according to the three-dimensional magnetic field data and three-dimensional attitude data at time t2; calculating the relative position pt2' of the first object relative to the second object at time t2 according to the three-dimensional acceleration data at time t2 and the relative speed v1 at time t1;

S46, comparing pt2 and pt2', and determining the relative position of the first object relative to the second object at time t2 is the mean value of pt2 and pt2' if the error between the two is within 1 cm, otherwise proceeding S47-S48;

S47, comparing the three-dimensional acceleration data at time t2 with the speed v1 at time t1, determining the relative position of the first object relative to the second object at time t2 is pt2 if both the speed v1 and the three-dimensional acceleration are approximately 0, otherwise the relative position of the first object relative to the second object at time t2 is pt2';

S48, adjusting the position of the first object and/or the second object, and repeating Steps S41-S46.

* * * * *